United States Patent [19]

Nyce

[11] 4,187,608
[45] Feb. 12, 1980

[54] IMPLANTABLE TEETH AND METHOD OF MAKING

[76] Inventor: Andrew C. Nyce, 1157 Shore Rd., Cape Elizabeth, Me. 04107

[21] Appl. No.: 648,307

[22] Filed: Jan. 12, 1976

Related U.S. Application Data

[63] Continuation-in-part of Ser. No. 407,085, Oct. 17, 1973, abandoned.

[51] Int. Cl.² ............................................. A61C 13/00
[52] U.S. Cl. .................................................... 433/201
[58] Field of Search .............. 32/10 A; 3/1; 128/92 C

[56] References Cited

U.S. PATENT DOCUMENTS

| | | | |
|---|---|---|---|
| 3,628,248 | 12/1971 | Kroder | 32/10 A |
| 3,787,900 | 1/1974 | McGee | 32/10 A |
| 3,808,606 | 5/1974 | Tronzo | 32/10 A |

OTHER PUBLICATIONS

"Sintered Fiber Metal Composites as a Basis for Attachment of Implants to Bones", by J. Galante et al., The Journal of Bone and Joint Surgery, vol. 53-A, No. 1, Jan. 1971, pp. 101–114.

*Primary Examiner*—Robert Peshock
*Attorney, Agent, or Firm*—Nicholas J. Aquilino

[57] ABSTRACT

An implantable tooth for humans is made by first extracting the natural tooth and producing therefrom an exact replica of at least the root portion of the tooth, formed of porous metal or ceramic with or without the application of a surface coating of dental porcelain or the like to the replica. It is then permanently implanted in the natural tooth socket with or without a stabilizing means anchored to the underlying alveolar bone. It is contemplated that the method is also applicable to a complete tooth with the porosity localized in the root area. More usually, a porcelain cap or the like would be used to top the root prosthesis.

12 Claims, 3 Drawing Figures

IMPLANTABLE TEETH AND METHOD OF MAKING

CROSS-REFERENCE TO RELATED APPLICATION

This application is a continuation-in-part of copending application Ser. No. 407,085 filed Oct. 17, 1973 and now abandoned.

BACKGROUND OF THE INVENTION

A need has been recognized for many years for an artificial tooth implant to successfully and permanently replace extracted or otherwise lost natural teeth in humans. It is understood that some experimentation in this area has been conducted on animals and humans utilizing plastic tooth implants with varying degrees of success. There is also some patented prior art relating to artificial tooth structures capable of being mechanically anchored in the natural tooth socket of humans with the assistance of bone-engaging threaded pins and the like. Some examples of the patented prior art are U.S. Pat. Nos. 448,745; 2,609,604; 3,435,526; and 2,347,567.

Generally speaking, prior art proposals along this line have not been widely adopted and have not been technically successful due to various factors existing in the human body and certain limitations inherent in the materials used for artificial tooth transplants.

Therefore, the object of this invention is to provide a completely successful artificial human tooth implant and method of producing which utilizes unique materials for the implant which are compatible with the normal growth of human tissue and bone structure so that the implant will become naturally anchored in the gum socket after installation, which may include initially an anchorage screw or pin for the underlying alveolar bone. More particularly, it has been discovered that certain porous metals and ceramics which can be molded by known techniques possess the physical characteristics which allow and facilitate successful periodontal fiber attachment and natural bone support without any apparent rejection by the human body. It appears that the periodontal fibers may penetrate deeply into the pores of the ceramic or like material for permanent natural anchorage of the prosthesis.

While it is contemplated ultimately that the implant may embody an exact replica of the whole tooth formed of suitable powdered metal, ceramic, pyrolytic carbon or the like with the porosity localized in the root portion, the invention at present is intended to be practiced in terms of a porous material replica of the root portion of the tooth topped by a porcelain cap or the like applied by conventional dental techniques.

The essential method embodying the invention consists of first extracting the natural tooth and immediately thereafter forming an exact flexible or rigid mold of the tooth, or one that is slightly oversize to compensate for shrinkage during casting, sintering or pressing. Next, the mold cavity which may or may not contain cast, wrought, or sintered shapes to which the powder will ultimately be bonded, is filled with an acceptable dental alloy, titanium, or a titanium alloy in the form of a powdered metal, followed by pressing, if required, and sintering. In the case of ceramics, the material is packed in a rubber mold and pressed and sintered or placed in a ceramic mold and vibrated with direct sintering. Following the formation of the molded replica of the tooth, it can be coated with porous alumina, titania or dental porcelain, and then placed directly in the natural tooth socket. By using narrowly sized fractions of metal, ceramic, or pyrolytic carbon, spherical or angular powder and combining these fractions so that binary, tertiary or quatinary mixtures of particles whose diameters are such that each smaller spherical or angular particle is 1/7 the diameter of the next larger particle diameter, high density powder mixtures with densities in excess of 80 percent prior to sintering can be achieved. For example, in a binary system, spheres of diameter $D_1$ would be mixed with spheres of diameter $D_2 = 1/7 \, D_1$. The high density powder mixes achieved exhibit very low sintered shrinkages.

The implant is preferably drilled and tapped and provided with a threaded pin extending below the tip of the root or roots into the underlying alveolar bone. This serves to stabilize the implant until the periodontal membrane and/or natural bone migrates into the surface pores of the implant.

The many advantages of the invention over the prior art will appear during the course of the following description taken in connection with the accompanying drawings which form a part of this application.

DETAILED DESCRIPTION

Figure 1:
FIG. 1 is a side elevational view of an extracted natural tooth.
Figure 2:
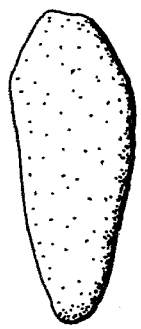
FIG. 2 is a similar view of a porous material replica of the extracted tooth.
Figure 3:
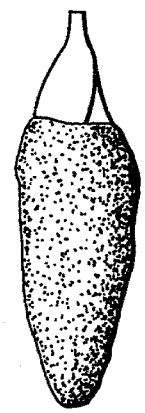
FIG. 3 is a similar view of the replica after coating with dental porcelain or similar material.

In accordance with the invention, a natural tooth is extracted from a patient and an exact replica is produced utilizing one of three basic methods.

According to a first method of producing the replica, vibratory compaction to high initial density and sintering of titanium spherical or angular particles using the 7 to 1 ratio principle to achieve high initial packed densities thereby minimizing shrinkage, in a ceramic mold is accomplished with known dental investment techniques. A cast, wrought or sintered blank of similar composition to the powder can be used to further minimize shrinkage by using it to take up some of the space in the ceramic mold.

Alternatively, the method may embody casting of vitallium, ceramco gold or ticonium dental alloys, again using conventional dental investment techniques, followed by application of a porous porcelain coating in the case of ceramco gold and plasma sprayed $TiO_2$ and $Al_2O_3$ in the case of ticonium and vitallium.

Thirdly, isostatic pressing and sintering of $TiO_2$, $Al_2O_3$, or titanium spherical or angular particles, carefully sized and blended using the 7 to 1 particle diameter ratio principle to achieve high packed density to minimize sintering shrinkage and to achieve controlled pore size, from exact replicas of extracted posterior or anterior teeth. Enlarged rubber replicas of the extracted teeth or sockets can be made by applying air pressure to rubber replicas to expand them, followed by filling with ceramic or metal powder and subsequent pressing.

In all of the above methods, a screw may be inserted through the root and into the underlying alveolar bone to anchor the root until connective periodontal tissue can grow into the surface pores. This screw can be of the same material as the powder and can in fact be placed in the mold cavity prior to introduction of the powder and prior to sintering.

Therefore, in essence, the method embodies (a) extracting the natural tooth from the patient; (b) forming either an exact mold of the tooth or tooth socket, or molds that are slightly oversize to compensate for shrinkage during casting, sintering and pressing; (c) filling the mold with a molten alloy of an acceptable dental type (vitallium, ticonium or ceramco gold) or similar suitable powdered metals; (d) pressing and sintering in the case of powdered metals, packed in a rubber mold, or directly sintering those powders vibrated in a ceramic mold; (e) coating of the resulting alloy tooth replica with porous alumina, titania or dental porcelain; and (f) drilling and tapping the replicated tooth for a long thin threaded pin extending below the tip of the root or roots and into the underlying alveolar bone. This will serve to stabilize the implant until the periodontal membrane and/or bone grows into the surface pores of the replicated implant.

The exact replica porous tooth implant possesses the three most important properties necessary for a successful tooth implant, namely, compatibility, strength, and ease of fabrication. Compatibility means minimum deterioration due to the corrosive and destructive forces present in the human body, minimum change in the host tissue, bone and fluid due to chemical reaction with the implant, and satisfactory functioning in service.

The implant formed by the invention is an exact replica of the extracted natural tooth (at least the root portion thereof) formed of material which possesses the proper porosity to allow fibers of the periodontal membrane to enter and grow into the pores for permanently anchoring the plant. Such an artificial tooth implant will give long service without complications and will function in very much the same manner as a healthy natural tooth.

It is to be understood that the form of the invention herewith shown and described is to be taken as a preferred example of the same, and that various changes in the shape, size and arrangement of parts may be resorted to, without departing from the spirit of the invention or scope of the subjoined claims.

What is claimed is:

1. A method of producing an artificial tooth for implantation in a natural tooth socket in the human body comprising the steps of mixing substantially spherical power metallurgical particles compatible with human body tissue of different size diameters such that the smaller particles fill the interstices of the next larger particles, molding an exact replica of an extracted tooth from said particles thereby creating a molded replica of the natural tooth having a porosity which allows the periodontal membrane to enter and grow into the pores of the implant and coating exterior portions of said molded replica with a finish having approximately the coloring of a natural tooth.

2. The method of claim 1 wherein said step of mixing said particles uses particles wherein the smaller particles are one-seventh the diameter of the next larger particles.

3. The method of claim 1 and the additional steps of pressing and sintering the powder metallurgical particles while in a mold.

4. The method of claim 1 wherein said mixture is a binary mixture.

5. The method of claim 1 wherein said mixture is a ternary mixture having three different size particles each size having a seven to one ratio between the larger and the next smaller particle size.

6. The method of claim 1 wherein said mixture is a quatenary mixture having four different size particles each size having a seven to one ratio between the larger and the next smaller particle size.

7. The method of claim 1 wherein said powder metallurgical particles are taken from the group consisting of vitallium, ticonium and ceramco gold in molten alloy form when placed in a mold cavity.

8. The method of claim 1 wherein said powder metallurgical particles are taken from the group consisting of aluminum oxide, titanium dioxide, titanium alloys or titanium particles which are sized and blended to achieve high packed density to minimize sintering shrinkage and to achieve controlled pore size.

9. An artificial human tooth implant comprising a porous molded human tooth replica formed of sintered spherical metallurgical particles, said particles being a mixture of different size diameters and being sized and blended to achieve high packed density and to minimize sintering shrinkage, the smaller of said particles fill the interstices of the larger particles when mixed and said particles being compatible with human tissue which allows fibers of the periodontal membrane to enter and grow into the pores of the implant.

10. An artificial human tooth implant wherein the smaller of said different size particles are one-seventh the diameter of the next larger particles.

11. An artificial human tooth implant according to claim 9 further including a coating of porous dental finishing material on a portion of the exterior of the implant.

12. An artificial human tooth implant according to claim 9 wherein said particles are taken from the group consisting of aluminum oxide, titanium dioxide, titanium or pyrolytic carbon.

* * * * *